(12) United States Patent
Mukai et al.

(10) Patent No.: US 12,384,863 B2
(45) Date of Patent: Aug. 12, 2025

(54) POLYMER, RESIST COMPOSITION, METHOD FOR MANUFACTURING SUBSTRATE HAVING PATTERN FORMED THEREIN, AND (METH)ACRYLIC ESTER AND PRODUCTION METHOD THEREFOR

(71) Applicant: Mitsubishi Chemical Corporation, Tokyo (JP)

(72) Inventors: Kazuaki Mukai, Tokyo (JP); Takeru Jo, Tokyo (JP); Yoshihiro Kamon, Tokyo (JP); Satoshi Sakuma, Tokyo (JP); Ryuichi Ansai, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 18/387,428

(22) Filed: Nov. 6, 2023

(65) Prior Publication Data
US 2024/0092956 A1 Mar. 21, 2024

Related U.S. Application Data

(62) Division of application No. 17/438,006, filed as application No. PCT/JP2020/013457 on Mar. 25, 2020, now Pat. No. 11,845,822.

(30) Foreign Application Priority Data

Mar. 27, 2019 (JP) .................. 2019-059909
Mar. 27, 2019 (JP) .................. 2019-059910
Mar. 27, 2019 (JP) .................. 2019-060490

(51) Int. Cl.
C08F 220/38 (2006.01)
C07D 333/48 (2006.01)
G03F 7/039 (2006.01)

(52) U.S. Cl.
CPC ........ *C08F 220/382* (2020.02); *C07D 333/48* (2013.01); *G03F 7/039* (2013.01)

(58) Field of Classification Search
CPC .................................... C08F 220/283
See application file for complete search history.

(56) References Cited

U.S. PATENT DOCUMENTS

| 3,257,319 A | 6/1966 | Raines et al. |
| 2004/0210082 A1 | 10/2004 | Furukawa et al. |
| 2006/0110677 A1 | 5/2006 | Houlihan et al. |

FOREIGN PATENT DOCUMENTS

| CN | 101061434 A | 10/2007 |
| EP | 1468981 A1 | 10/2004 |
| JP | 2001-201868 A | 7/2001 |
| JP | 2004-315464 A | 11/2004 |
| JP | 2007-153763 A | 6/2007 |
| JP | 2008-521039 A | 6/2008 |
| JP | 2009-196944 A | 9/2009 |
| JP | 2011-184390 A | 9/2011 |
| JP | 2012-150170 A | 8/2012 |
| JP | 2012-234166 A | 11/2012 |
| JP | 2012-252244 A | 12/2012 |
| KR | 20070117539 A * | 12/2007 |
| WO | 2005/111097 A1 | 11/2005 |

OTHER PUBLICATIONS

International Search Report issued in corresponding International Patent Application No. PCT/JP2020/013457 dated Jun. 9, 2020.
Office Action issued in related Taiwanese Patent Application No. 109110089 dated Jun. 12, 2023.
Office Action issued in related Chinese Patent Application No. 202080023085.9 dated Apr. 17, 2023.
Office Action issued in related Japanese Patent Application No. 2021-509539 dated May 23, 2023.
English translation of Written Opinion issued in corresponding International Patent Application No. PCT/JP2020/013457 dated Jun. 9, 2020.
Office Action issued Nov. 28, 2023 for Taiwanese Patent Application No. 109110089.
Office Action issued in corresponding Japanese Patent Application No. 2023-148444 dated Sep. 3, 2024.
Office Action issued in corresponding Korean Patent Application No. 10-2021-7029891, dated Dec. 17, 2024.

* cited by examiner

*Primary Examiner* — Amanda C. Walke
(74) *Attorney, Agent, or Firm* — Morgan, Lewis & Bockius LLP

(57) ABSTRACT

Provided is a polymer including a constituent unit (1) based on a monomer represented by Formula (1), in which a content of a constituent unit based on a monomer having a polycyclic structure is 35 mol % or less. In Formula (1), $R^1$ represents a hydrogen atom or a methyl group, $A^1$ represents a linking group including an ester bond, or a single bond, where $A^1$ has no tertiary carbon atom, and $Z^1$ represents an atomic group forming a sulfur-containing cyclic hydrocarbon group having 3 to 6 carbon atoms, which includes a carbon atom bonded to $A^1$, and $-SO_2-$.

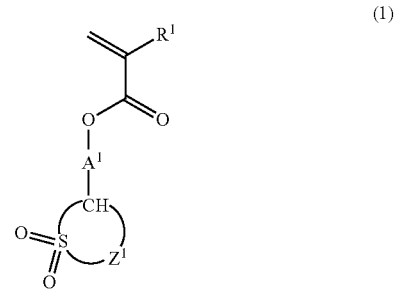

17 Claims, No Drawings

POLYMER, RESIST COMPOSITION, METHOD FOR MANUFACTURING SUBSTRATE HAVING PATTERN FORMED THEREIN, AND (METH)ACRYLIC ESTER AND PRODUCTION METHOD THEREFOR

TECHNICAL FIELD

The present invention relates to a polymer, a resist composition including the polymer, a method for manufacturing a substrate having a pattern therein using the resist composition, a (meth)acrylic ester, and a production method of the (meth)acrylic ester.

Priority is claimed on Japanese Patent Application No. 2019-059909, Japanese Patent Application No. 2019-059910, and Japanese Patent Application No. 2019-060490, filed Mar. 27, 2019, the contents of which are incorporated herein by reference.

BACKGROUND ART

A (meth)acrylic ester containing a sulfonyl group (hereinafter, may be referred to as a "sulfonyl group-containing (meth)acrylic ester") is known as a sulfur-containing monomer. A polymer obtained by homopolymerizing the sulfonyl group-containing (meth)acrylic ester or a copolymer obtained by copolymerizing the sulfonyl group-containing (meth)acrylic ester with another monomer may be used, for example, as a material having a high dielectric constant, a material having a high refractive index, or a medical adhesive having an anti-inflammatory effect.

As a production method of such a sulfonyl group-containing (meth)acrylic ester, a method by ester exchange reaction between a (meth)acrylic ester and an alcohol is known (for example, Patent Document 1).

As an exposure light source of lithography used for manufacturing semiconductors, the wavelength has been shortened, and as a next-generation exposure light source, mass production of semiconductor devices using an ArF excimer laser having a wavelength of 193 nm or extreme ultraviolet (EUV) having a wavelength of 13.5 nm, which has higher energy, is progressing.

It is desirable that a resist polymer adopted to these include a polar group from the viewpoint of adhesiveness to a substrate and affinity for a polar solvent. In the related art, as a monomer including such a polar group, a (meth)acrylic ester containing a lactone group has been widely used.

The sulfonyl group-containing (meth)acrylic ester has high polarity, so that it is expected that the sulfonyl group-containing (meth)acrylic ester can also be adopted as the monomer (raw material monomer) constituting the resist polymer.

When producing the resist polymer using the sulfonyl group-containing (meth)acrylic ester as the monomer, in a case where a high-molecular-weight substance is mixed in the sulfonyl group-containing (meth)acrylic ester, the high-molecular-weight substance may be insoluble matter and defects may occur during development. Therefore, it is necessary to reduce the content of the high-molecular-weight substance as much as possible.

As a resist composition which can be suitably used for shortening the wavelength of irradiation light and miniaturizing a pattern in lithography technology, a chemically amplified resist composition is known. The chemically amplified resist composition includes a resist polymer from which an acid-eliminating group is eliminated by action of an acid, and a photoacid generator.

In recent years, pattern miniaturization has progressed rapidly, and it is desired to develop a resist material capable of further improving various lithography characteristics such as sensitivity, pattern formability, and line width roughness (LWR).

In Comparative Examples of Patent Document 2, a polymer obtained by polymerizing a mixture of a monomer represented by Formula (a1-1-2), a monomer represented by Formula (a2-1-1), a monomer represented by Formula (a3-1-1), and a monomer represented by Formula (I-2) in a molar ratio of 30:20:40:10 is disclosed. In addition, when a resist pattern is formed using the resist composition containing the polymer and the acid generator, it is disclosed that roughness occurs on the side surface of the pattern and the line width roughness (LWR) is inferior.

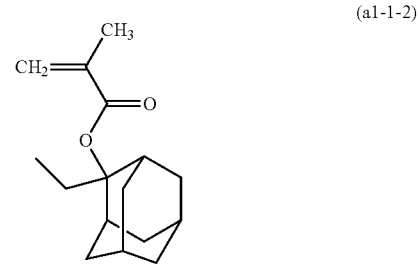

(a1-1-2)

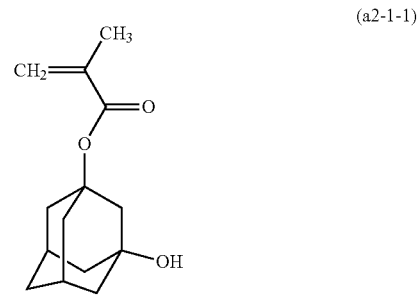

(a2-1-1)

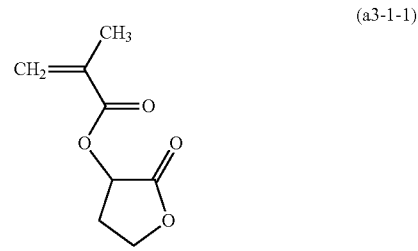

(a3-1-1)

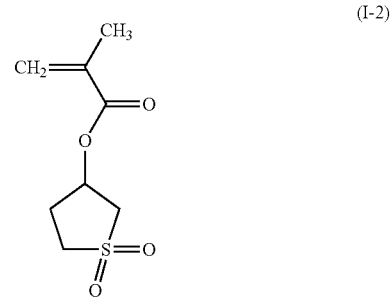

(I-2)

CITATION LIST

Patent Documents

[Patent Document 1]
  Japanese Unexamined Patent Application, First Publication No. 2007-153763
[Patent Document 2]
  Japanese Unexamined Patent Application, First Publication No. 2012-234166

SUMMARY OF INVENTION

Technical Problem

When a sulfonyl group-containing (meth)acrylic ester is produced by an ester exchange method as in Patent Document 1, in order to tilt the equilibrium toward the product, alcohols, such as methanol, produced by the reaction are extracted by distillation. Therefore, it is necessary to raise the reaction temperature to a high temperature.

As a result of studies, the present inventors have found that the sulfonyl group-containing (meth)acrylic ester is highly polymerizable, and when the sulfonyl group-containing (meth)acrylic ester is exposed to a high temperature in the ester exchange reaction, a high-molecular-weight substance is produced by the polymerization of the sulfonyl group-containing (meth)acrylic ester.

Patent Document 1 discloses that the product is purified by recrystallization, washing, or the like, but with such a method, the high-molecular-weight substance cannot be sufficiently removed.

In addition, in a resist composition including a polymer having an acid-eliminating group, improvement of LWR can be expected by improving solubility of the polymer in a developer.

An object of the present invention is to provide a polymer having excellent solubility in a developer, to provide a resist composition including the polymer, to provide a method for manufacturing a substrate having a pattern therein using the resist composition, to provide a (meth)acrylic ester in which a high-molecular-weight substance is reduced, and to provide a production method of a (meth)acrylic ester in which a high-molecular-weight substance is reduced.

Solution to Problem

The present invention has the following aspects.

[1] A polymer including:
  a constituent unit (1) based on a monomer represented by Formula (1),
  in which a content of a constituent unit based on a monomer having a polycyclic structure is 35 mol % or less.

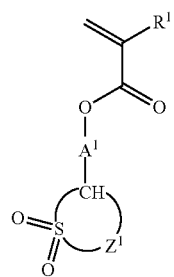

(1)

In Formula (1), $R^1$ represents a hydrogen atom or a methyl group, $A^1$ represents a linking group including an ester bond, or a single bond, where $A^1$ has no tertiary carbon atom, and $Z^1$ represents an atomic group forming a sulfur-containing cyclic hydrocarbon group having 3 to 6 carbon atoms, which includes a carbon atom bonded to $A^1$, and —$SO_2$—.

[2] The polymer according to [1], further including:
  a constituent unit (2) having an acid-eliminating group.
[3] The polymer according to [2],
  in which the constituent unit (2) includes a constituent unit (2i) which has an acid-eliminating group including an alicyclic hydrocarbon group.
[4] The polymer according to [3],
  in which the constituent unit (2) includes a constituent unit (2ii) which has an acid-eliminating group including a monocyclic alicyclic hydrocarbon group.
[5] The polymer according to any one of [1] to [4],
  in which the constituent unit (1) is 15 mol % or more with respect to all constituent units.
[6] The polymer according to any one of [1] to [5], further including:
  a constituent unit (3) having a lactone skeleton.
[7] A resist composition including:
  the polymer according to any one of [1] to [6]; and
  a compound generating acid by irradiation with active light or radiation.
[8] A method for manufacturing a substrate having a pattern formed therein, including:
  a step of applying the resist composition according to [7] to a surface of a substrate to be processed to form a resist film;
  a step of exposing the resist film; and
  a step of developing the exposed resist film with a developer.
[9] A production method of a (meth)acrylic ester represented by Formula (1x), including:
  a step 1: step of performing an ester exchange reaction between an alcohol represented by Formula (2x) and a (meth)acrylic ester represented by Formula (3x) to obtain a solution including a (meth)acrylic ester (1x) represented by Formula (1x); and
  a step 2: step of adding a poor solvent to the solution including the (meth)acrylic ester (1x) obtained in the step 1 to precipitate a high-molecular-weight substance, and removing the high-molecular-weight substance.

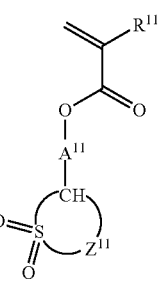

(1x)

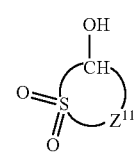

(2x)

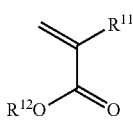

(3x)

In Formula (1x), $R^{11}$ represents a hydrogen atom or a methyl group, $A^{11}$ represents a linking group including an ester bond, or a single bond, where $A^{11}$ has no tertiary carbon atom, and $Z^{11}$ represents an atomic group forming a sulfur-containing cyclic hydrocarbon group having 3 to 6 carbon atoms, which includes a carbon atom bonded to $A^{11}$, and —$SO_2$—.

In Formula (2x), $Z^{11}$ represents an atomic group forming a sulfur-containing cyclic hydrocarbon group having 3 to 6 carbon atoms, which includes a carbon atom bonded to a hydroxy group, and —$SO_2$—.

In Formula (3x), $R^{11}$ represents a hydrogen atom or a methyl group, and $R^{12}$ represents a linear or branched alkyl group having 1 to 10 carbon atoms.

[10] The production method of a (meth)acrylic ester according to [9],
in which a hydrocarbon solvent is used as the poor solvent in the step 2.

[11] A (meth)acrylic ester represented by Formula (1x), in which a content of a high-molecular-weight substance having a molecular weight of 5000 or more is 0.1 mass % or less.

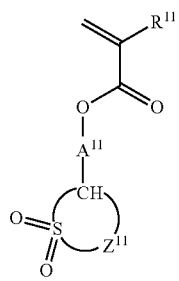

(1x)

In Formula (1x), $R^{11}$ represents a hydrogen atom or a methyl group, $A^{11}$ represents a linking group including an ester bond, or a single bond, where $A^{11}$ has no tertiary carbon atom, and $Z^{11}$ represents an atomic group forming a sulfur-containing cyclic hydrocarbon group having 3 to 6 carbon atoms, which includes a carbon atom bonded to $A^{11}$, and —$SO_2$—.

Advantageous Effects of Invention

According to the present invention, it is possible to provide a polymer having favorable solubility in a developer, a resist composition including the polymer, and a method for manufacturing a substrate having a pattern formed therein using the resist composition.

According to the present invention, it is possible to provide a sulfonyl group-containing (meth)acrylic ester in which a high-molecular-weight substance is reduced.

DESCRIPTION OF EMBODIMENTS

Embodiments of the present invention will be described in detail below.

Definitions of the following terms apply throughout the specification and claims.

In the present specification, "(meth)acrylic acid" means one or both of acrylic acid and methacrylic acid.

In the present specification, "constituent unit" means an atomic group formed by a polymerization reaction of monomers.

In the present specification, a monomer represented Formula (1) may be referred to as a monomer (1). The same applies to monomers represented by other formulae.

In the present specification, a compound represented by Formula (1) may be referred to as a compound (1). The same applies to compounds represented by other formulae.

<Polymer>

A polymer according to the present embodiment (hereinafter, also referred to as a "polymer A") includes a constituent unit (1) based on a monomer (1) represented by Formula (1). The content of a constituent unit based on a monomer having a polycyclic structure is 35 mol % or less with respect to all constituent units of the polymer A.

It is preferable that the polymer A further include one or more constituent units (2) having an acid-eliminating group. The polymer A may include one or more constituent units other than the constituent units (1) and (2).

The polymer A is suitable as a resist polymer.

[Constituent Unit (1)]

The constituent unit (1) is a constituent unit formed by cleaving an ethylenic double bond of the monomer (1).

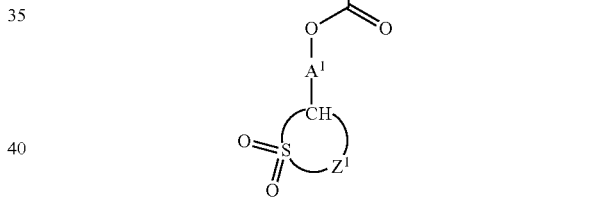

(1)

In Formula (1), $R^1$ represents a hydrogen atom or a methyl group.

$A^1$ is a linking group including an ester bond, or a single bond. However, $A^1$ has no tertiary carbon atom. Examples of the linking group include -$A^2$-C(=O)O— and -$A^3$-O—C(=O)—. $A^2$ and $A^3$ are divalent chain-like hydrocarbon groups having 1 to 5 carbon atoms. The chain-like hydrocarbon groups as $A^2$ and $A^3$ may be linear or branched. $A^2$ and $A^3$ are preferably an alkylene group having 1 to 3 carbon atoms. $A^2$ and $A^3$ have no tertiary carbon atom.

$Z^1$ is an atomic group forming a sulfur-containing cyclic hydrocarbon group (4-membered ring to 7-membered ring) having 3 to 6 carbon atoms, which includes a carbon atom bonded to $A^1$, and —$SO_2$—. From the viewpoint of the stability of the cyclic structure, the sulfur-containing cyclic hydrocarbon group preferably has 4 to 6 carbon atoms. In addition, a substituent may be bonded to a carbon atom constituting a ring of the sulfur-containing cyclic hydrocarbon group. Examples of the substituent include a linear or branched alkyl group having 1 to 10 carbon atoms, a hydroxy group, an amino group, an aldehyde group, a chloro group, a bromo group, and an iodo group.

As the monomer (1), an aspect in which a substituent is not bonded to the carbon atom constituting the ring of the sulfur-containing cyclic hydrocarbon group, or an alkyl group having 1 to 6 carbon atoms is bonded thereto as a substituent is preferable. The monomer of this aspect is represented by Formula (1').

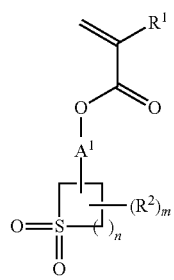

(1')

In Formula (1'), $R^1$ and $A^1$ are the same as $R^1$ and $A^1$ in Formula (1).

n represents an integer of 1 to 4. A heterocycle bonded to $A^1$ is, for example, a 4-membered ring when n is 1, and a 7-membered ring when n is 4. From the viewpoint of stability and ease of synthesis, n is preferably 2.

$R^2$ represents a substituent bonded to a carbon atom constituting the above-described heterocycle. However, $R^2$ is not bonded to the carbon atom bonded to $A^1$.

m of $R^2$ each independently represents an alkyl group having 1 to 6 carbon atoms. The alkyl group may be linear or branched. When m is 2 or more, a plurality of $R^2$ existing in one molecule may be the same as or different from each other.

m is an integer of 0 or more and (n+1) or less, and is preferably an integer of 0 or more and n or less, more preferably 0 or 1, and most preferably 0.

Examples of a group bonded to $A^1$ include groups represented by Formulae (1a) to (1d). * in the formulae represents a bonding position to $A^1$.

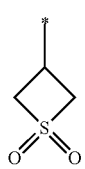

(1a)

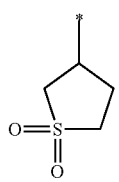

(1b)

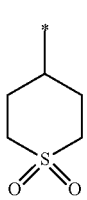

(1c)

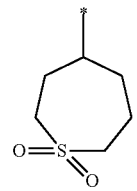

(1d)

As the monomer (1), an aspect in which $R^1$ is a hydrogen atom or a methyl group, $A^1$ is a single bond, and any one of the groups represented by Formulae (1a) to (1d) is bonded to $A^1$ is preferable.

Among the groups represented by Formulae (1a) to (1d), from the viewpoint of stability and ease of synthesis, the group represented by Formula (1b) is particularly preferable.

The constituent unit (1) included in the polymer A may be one kind or two or more kinds.

The constituent unit (1) is preferably 15 mol % or more, more preferably 20 mol % or more, and still more preferably 25 mol % or more with respect to all constituent units of the polymer A. From the viewpoint of sensitivity and resolution, the upper limit is preferably 70 mol % or less, more preferably 60 mol % or less, and still more preferably 50 mol % or less.

For example, the constituent unit (1) is preferably 15 to 70 mol %, more preferably 20 to 60 mol %, still more preferably 25 to 60 mol %, and particularly preferably 25 to 50 mol % with respect to all constituent units of the polymer A.

[Constituent Unit (2)]

The constituent unit (2) is a constituent unit based on a monomer (hereinafter, also referred to as a monomer (2)) having an acid-eliminating group. The acid-eliminating group is a group having a bond which is cleaved by action of an acid, and is a group in which a part or all of the acid-eliminating group is eliminated from the polymer by the cleavage of the bond. In a positive type chemically amplified resist composition, by heating after exposure, an acid-eliminating group of the polymer in an exposed portion reacts with the acid to be eliminated, and the polymer is soluble in an alkaline developer.

The monomer (2) is preferably a (meth)acrylic ester compound. As the (meth)acrylic ester compound having an acid-eliminating group, a known compound can be used.

From the viewpoint of dry etching resistance in the lithography process, the monomer (2) preferably includes a (meth)acrylic ester compound which has an acid-eliminating group including an alicyclic hydrocarbon group.

The above-described alicyclic hydrocarbon group may be monocyclic or polycyclic. The above-described alicyclic hydrocarbon group may include a heteroatom. The above-described heteroatom is preferably one or more atoms selected from the group consisting of O, S, and N. The number of atoms constituting the ring is preferably 5 to 22.

From the viewpoint that sensitivity and resolution of a resist are excellent, it is more preferably an acrylic ester which has a tertiary carbon atom at a bonding site with an oxygen atom constituting the ester bond of acrylic ester. Specific examples thereof include monomers (2-1) to (2-4) of the following formulae.

In particular, from the viewpoint that, when combined with the constituent unit (1), the effect of improving solubility in a developer can be easily obtained, the monomer (2-4) is more preferable.

(2-1)
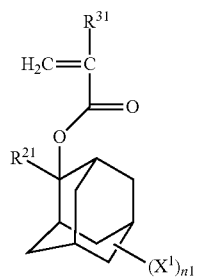

(2-2)
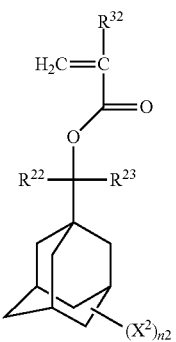

(2-3)
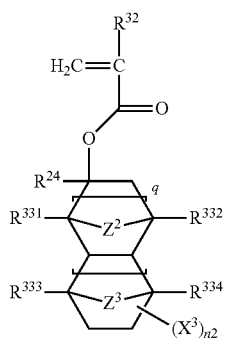

(2-4)
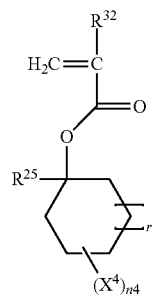

In Formulae (2-1) to (2-4), $R^{31}$, $R^{32}$, $R^{33}$, and $R^{34}$ each independently represents a hydrogen atom or a methyl group.

$R^{21}$, $R^{24}$, and $R^{25}$ each independently represents an alkyl group having 1 to 5 carbon atoms. The alkyl group may be linear or branched.

$R^{22}$ and $R^{23}$ each independently represents an alkyl group having 1 to 3 carbon atoms. The alkyl group may be linear or branched.

$R^{331}$, $R^{332}$, $R^{333}$, and $R^{334}$ each independently represents a hydrogen atom or an alkyl group having 1 to 6 carbon atoms. The alkyl group may be linear or branched.

$X^1$, $X^2$, $X^3$, and $X^4$ each independently represents an alkyl group having 1 to 6 carbon atoms. The alkyl group may be linear or branched.

n1, n2, n3, and n4 each independently represents an integer of 0 to 4. When n1, n2, n3, or n4 is 2 or more, a plurality of $X^1$, $X^2$, $X^3$, or $X^4$ existing in one molecule may be the same as or different from each other.

$Z^2$ and $Z^3$ each independently represents —O—, —S—, —NH—, or —(CH$_2$)$_k$—. k represents an integer of 1 to 6.

q represents 0 or 1.

r represents an integer of 0 to 3.

The constituent unit (2) included in the polymer A may be one kind or two or more kinds.

The constituent unit (2) is preferably 20 to 80 mol %, more preferably 30 to 70 mol %, and still more preferably 40 to 60 mol % with respect to all constituent units of the polymer A. In a case of being the lower limit value or more of the above-described range, favorable sensitivity can be easily obtained, and in a case of being the upper limit value or less, it is easy to obtain a favorable balance as a resist and it is easy to obtain favorable adhesiveness to a substrate.

The constituent unit (2) preferably includes a constituent unit (2i) which has an acid-eliminating group including an alicyclic hydrocarbon group. The above-described alicyclic hydrocarbon group may be monocyclic or polycyclic. The above-described alicyclic hydrocarbon group may include a heteroatom. The above-described heteroatom is preferably one or more atoms selected from the group consisting of O, S, and N. The number of atoms constituting the ring is preferably 5 to 22.

The content of the constituent unit (2i) is preferably 25 mol % or more, more preferably 35 mol % or more, still more preferably 50 mol % or more, and particularly preferably 75 mol % or more with respect to the total number of moles of the constituent unit (2). The content of the constituent unit (2i) may be 100 mol %. When the content of the constituent unit (2i) is the above-described lower limit value or more, when combined with the constituent unit (1), the effect of improving solubility in a developer can be easily obtained.

The constituent unit (2) more preferably includes a constituent unit (2ii) which has an acid-eliminating group including a monocyclic alicyclic hydrocarbon group. The above-described monocyclic alicyclic hydrocarbon group preferably does not include a heteroatom. The number of atoms constituting the ring of the above-described monocyclic alicyclic hydrocarbon group is more preferably 5 to 8 and still more preferably 5 or 6. For example, a constituent unit based on the above-described monomer (2-4) is more preferable.

The content of the constituent unit (2ii) is preferably 25 mol % or more, more preferably 35 mol % or more, still more preferably 50 mol % or more, and particularly preferably 75 mol % or more with respect to the total number of moles of the constituent unit (2). The content of the constituent unit (2ii) may be 100 mol %. When the content of the constituent unit (2ii) is the above-described lower limit value or more, when combined with the constituent unit (1), the effect of improving solubility in a developer can be easily obtained.

The content of a constituent unit based on a monomer having a polycyclic structure is 35 mol % or less, more preferably 30 mol % or less with respect to all constituent units of the polymer A. When the constituent unit having a polycyclic structure is 35 mol % or less, solubility of the polymer A in a developer is excellent.

[Other Constituent Units]

As other constituent units, a known constituent unit in the chemically amplified resist composition can be used.

Examples thereof include a constituent unit having a lactone skeleton and a constituent unit having a hydrophilic group.

(Constituent Unit Having Lactone Skeleton (Hereinafter, Also Referred to as Lactone Unit))

The lactone skeleton means a monocyclic or polycyclic atomic group including a ring having —O—C(=O)—. The above-described ring having —O—C(=O)— may be a ring having —C(=O)—O—C(=O)—.

The lactone skeleton is preferably a 4- to 20-membered ring and more preferably a 5- to 10-membered ring.

The lactone skeleton may be a monocycle having only a lactone ring, or an aromatic or non-aromatic hydrocarbon ring or heterocycle may be condensed on the lactone ring.

As the monomer having a lactone skeleton, a (meth)acrylic ester compound is preferable. In particular, from the viewpoint that adhesiveness to a substrate or the like is excellent, at least one selected from the group consisting of (meth)acrylic ester having a substituted or unsubstituted δ-valerolactone ring and (meth)acrylic ester having a substituted or unsubstituted γ-butyrolactone ring is preferable, and a monomer having an unsubstituted γ-butyrolactone ring is particularly preferable.

Specific examples of the monomer having a lactone skeleton include β-(meth)acryloyloxy-β-methyl-δ-valerolactone, 4,4-dimethyl-2-methylene-γ-butyrolactone, β-(meth)acryloyloxy-γ-butyrolactone, β-(meth)acryloyloxy-β-methyl-γ-butyrolactone, α-(meth)acryloyloxy-γ-butyrolactone, 2-(1-(meth)acryloyloxy)ethyl-4-butanolide, (meth)acrylic pantoyl lactone, 5-(meth)acryloyloxy-2,6-norbornane carbolactone, 8-methacryloxy-4-oxatricyclo[5.2.1.0$^{2,6}$]decan-3-one, and 9-methacryloxy-4-oxatricyclo[5.2.1.0$^{2,6}$]decan-3-one.

The lactone unit included in the polymer A may be one kind or two or more kinds.

When the polymer A includes the lactone unit, the content thereof is preferably 10 to 70 mol %, more preferably 20 to 60 mol %, and still more preferably 30 to 50 mol % with respect to all constituent units of the polymer A. In a case of being within the above-described range, the effect of improving adhesiveness to a substrate can be easily obtained.

(Constituent Unit Having Hydrophilic Group (Hereinafter, Also Referred to as Hydrophilic Unit))

The "hydrophilic group" in the present specification is one or more selected from the group consisting of —C(CF$_3$)$_2$—OH, a hydroxy group, a cyano group, a methoxy group, a carboxy group, and an amino group.

As the monomer having a hydrophilic group, a (meth)acrylic ester compound or a styrene derivative having a hydroxy group is preferable.

Specific examples of the monomer having a hydrophilic group include (meth)acrylic acid, 2-hydroxyethyl (meth)acrylate, 3-hydroxypropyl (meth)acrylate, 2-hydroxy-n-propyl (meth)acrylate, 4-hydroxybutyl (meth)acrylate, 3-hydroxyadamantyl (meth)acrylate, 2- or 3-cyano-5-norbornyl (meth)acrylate, 2-cyanomethyl-2-adamantyl (meth)acrylate, p-hydroxystyrene, and dihydroxystyrene.

From the viewpoint of adhesiveness to a substrate or the like, 3-hydroxyadamantyl (meth)acrylate, 3,5-dihydroxyadamantyl (meth)acrylate, 2- or 3-cyano-5-norbornyl (meth)acrylate, 2-cyanomethyl-2-adamantyl (meth)acrylate, or the like is preferable.

The hydrophilic unit included in the polymer A may be one kind or two or more kinds.

The constituent unit having a hydrophilic group contributes to improvement of wettability of the polymer A to a developer. The content of the constituent unit having a hydrophilic group is preferably 0 to 40 mol %, more preferably 5 to 30 mol %, and still more preferably 10 to 20 mol % with respect to all constituent units of the polymer A. In a case of being within the above-described range, a favorable balance as a resist can be easily obtained.

Examples of a preferred aspect of the polymer A include the following aspects (i) to (iv).

(i) polymer including the constituent unit (1) and the constituent unit (2), in which the constituent unit (1) is 15 to 70 mol % and the constituent unit (2) is 20 to 80 mol % with respect to all constituent units, and the total thereof is 35 to 100 mol %

(ii) polymer including the constituent unit (1), the constituent unit (2), and the lactone unit, in which, with respect to all constituent units, the constituent unit (1) is 15 to 70 mol %, the lactone unit is 10 to 70 mol %, the total of the constituent unit (1) and the lactone unit is 25 to 85 mol %, the constituent unit (2) is 20 to 80 mol %, and the total of the constituent unit (1), the constituent unit (2), and the lactone unit is 45 to 100 mol %

(iii) polymer including the constituent unit (1), the constituent unit (2), and the hydrophilic unit, in which, with respect to all constituent units, the constituent unit (1) is 15 to 70 mol %, the hydrophilic unit is 0 to 40 mol %, the total of the constituent unit (1) and the hydrophilic unit is 15 to 80 mol %, the constituent unit (2) is 20 to 80 mol %, and the total of the constituent unit (1), the constituent unit (2), and the hydrophilic unit is 35 to 100 mol %

(iv) polymer including the constituent unit (1), the constituent unit (2), the lactone unit, and the hydrophilic unit, in which, with respect to all constituent units, the constituent unit (1) is 15 to 70 mol %, the lactone unit is 10 to 70 mol %, the hydrophilic unit is 0 to 40 mol %, the total of the constituent unit (1), the lactone unit, and the hydrophilic unit is 25 to 85 mol %, the constituent unit (2) is 25 to 80 mol %, and the total of the constituent unit (1), the constituent unit (2), the lactone unit, and the hydrophilic unit is 50 to 100 mol %

The polymer A can be produced, for example, by a solution polymerization method in which a monomer is radically polymerized using a polymerization initiator in the presence of a polymerization solvent.

The weight average molecular weight of the polymer A is preferably 1,000 to 100,000, more preferably 3,000 to 50,000, and still more preferably 5,000 to 30,000.

<Resist Composition>

A resist composition according to the present embodiment preferably includes the polymer A, a resist solvent, and a compound generating acid by irradiation with active light or radiation. One kind of the polymer A may be used, or two or more kinds thereof may be used in combination.

The content of the polymer A with respect to the resist composition (excluding the solvent) is not particularly limited, but is preferably 70 to 99.9 mass %.

Examples of the resist solvent include cyclopentanone, cyclohexanone, propylene glycol monomethyl ether acetate (PGMEA), and propylene glycol monomethyl ether (PGME). One kind of the resist solvent may be used, or two or more kinds thereof may be used in combination.

The amount of the resist solvent used depends on a thickness of a resist film to be formed, but is preferably 100 to 10,000 parts by mass with respect to 100 parts by mass of the polymer A.

The compound generating acid by irradiation with active light or radiation can be optionally selected from those which can be used as a photoacid generator of the chemically amplified resist composition. One kind of the photoacid generator may be used, or two or more kinds thereof may be used in combination.

Examples of the photoacid generator include onium salt compounds, sulfonimide compounds, sulfone compounds, sulfonic acid ester compounds, quinonediazide compounds, and diazomethane compounds.

The amount of the photoacid generator used is preferably 0.1 to 20 parts by mass and more preferably 0.5 to 10 parts by mass with respect to 100 parts by mass of the polymer A.

The resist composition may include various additives such as a nitrogen-containing compound, an acid compound (organic carboxylic acid, and oxo acid of phosphorus or a derivative thereof), a surfactant, other quenchers, a sensitizer, an anti-halation agent, a storage stabilizer, and a defoamer, as necessary. As the above-described additives, those known in the field of resist compositions can be used.

<Method for Manufacturing Substrate Having Pattern Formed Therein>

An example of a method for manufacturing a substrate having a pattern formed therein according to the present embodiment will be described.

First, the resist composition is applied to a surface (surface to be processed) of a substrate to be processed such as a silicon wafer by spin coating or the like. The substrate to be processed, to which the resist composition has been applied, is dried by a baking treatment (pre-baking) or the like to form a resist film on the substrate.

Next, the resist film is irradiated with light having a wavelength of 250 nm or less through a photomask to form a latent image (exposure). As irradiation light, KrF excimer laser, ArF excimer laser, $F_2$ excimer laser, or EUV excimer laser is preferable, and ArF excimer laser is particularly preferable. In addition, the resist film may be irradiated with an electron beam.

In addition, a liquid immersion exposure in which the resist film is irradiated with light in a state in which a high refractive index liquid such as pure water, perfluoro-2-butyl tetrahydrofuran, and perfluorotrialkylamine is interposed between the resist film and a final lens of an exposure apparatus may be performed.

After the exposure, heat treatment (post-exposure baking, PEB) is performed as appropriate, and a developer is brought into contact with the resist film to dissolve a part of the resist film. In the positive development process, an exposed portion is dissolved and removed with an alkaline developer.

In the polymer A, the bond of the acid-eliminating group is cleaved by acid generated by the exposure, and the dissolution rate of the exposed portion in the alkaline developer is increased.

As the alkaline developer, an alkaline aqueous solution is used. Examples thereof include aqueous solutions of inorganic alkalis such as sodium hydroxide, potassium hydroxide, sodium carbonate, sodium silicate, sodium metasilicate, and aqueous ammonia; primary amines such as ethylamine and n-propylamine; secondary amines such as diethylamine and di-n-butylamine; tertiary amines such as triethylamine and methyldiethylamine; alcohol amines such as dimethylethanolamine and triethanolamine; quaternary ammonium salts such as tetramethylammonium hydroxide and tetraethylammonium hydroxide; and cyclic amines such as pyrrole and piperidine.

After the development, the substrate is appropriately rinsed with pure water or the like. In this way, a resist pattern is formed on the substrate to be processed.

The substrate having a resist pattern therein is appropriately heat-treated (post-baked) to strengthen the resist, and a portion without the resist is selectively dry-etched.

After dry etching, the resist is removed with a release agent to obtain a substrate having a fine pattern therein.

<(Meth)Acrylic Ester>

A (meth)acrylic ester according to the present embodiment is a sulfonyl group-containing (meth)acrylic ester (compound (1x)) represented by Formula (1x), in which the content of a high-molecular-weight substance having a molecular weight of 5000 or more is 0.1 mass % or less.

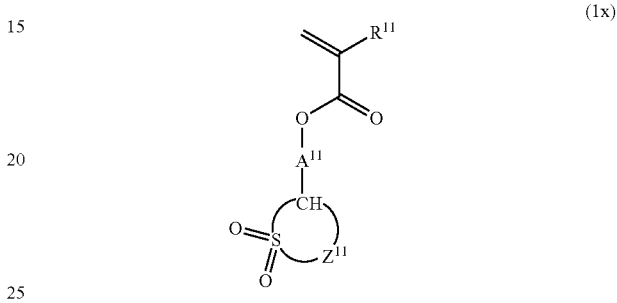

In Formula (1x), $R^{11}$ represents a hydrogen atom or a methyl group, $A^{11}$ represents a linking group including an ester bond, or a single bond, where $A^{11}$ has no tertiary carbon atom, and $Z^{11}$ represents an atomic group forming a sulfur-containing cyclic hydrocarbon group having 3 to 6 carbon atoms, which includes a carbon atom bonded to $A^{11}$, and —$SO_2$—.

Here, the (meth)acrylic ester according to the present embodiment, in which the content of the high-molecular-weight substance having a molecular weight of 5000 or more is defined, may be referred to as a "(meth)acrylic ester composition" instead of the "(meth)acrylic ester", but in the (meth)acrylic ester according to the present embodiment, the high-molecular-weight substance (hereinafter, may be simply referred to as a "high-molecular-weight substance") having a molecular weight of 5000 or more is contained in a very small amount of 0.1 mass % or less, or the content thereof is below a detection limit and the high-molecular-weight substance is almost non-existent. In addition, since (meth)acrylic ester having a high-molecular-weight substance content of 0.1 mass % or less is regarded as a "(meth)acrylic ester product" and is further used for various purposes, in the present embodiment, such a (meth)acrylic ester containing a very small amount or almost no high-molecular-weight substance is referred to as the "(meth)acrylic ester".

In addition, as described above, having a high-molecular-weight substance content of 0.1 mass % includes the high-molecular-weight substance content being below the detection limit in the analysis of the high-molecular-weight substance and being substantially 0 mass %.

[Compound (1x)]

In Formula (1x), $A^{11}$ is a linking group including an ester bond, or a single bond. However, $A^{11}$ has no tertiary carbon atom. The linking group including an ester bond as $A^{11}$ is the same as the linking group including an ester bond as $A^1$ described above. From the viewpoint of easy availability of raw materials and ease of synthesis, $A^{11}$ is preferably a single bond.

$R^{11}$ is a hydrogen atom or a methyl group, and is preferably a methyl group.

$Z^{11}$ is an atomic group forming a sulfur-containing cyclic hydrocarbon group (4-membered ring to 7-membered ring) having 3 to 6 carbon atoms, which includes a carbon atom bonded to $A^{11}$, and —$SO_2$—. From the viewpoint of the stability of the cyclic structure, the sulfur-containing cyclic hydrocarbon group preferably has 4 to 6 carbon atoms. In addition, a substituent may be bonded to a carbon atom constituting a ring of the sulfur-containing cyclic hydrocarbon group. Examples of the substituent include a linear or branched alkyl group having 1 to 10 carbon atoms, a hydroxy group, an amino group, an aldehyde group, a chloro group, a bromo group, and an iodo group.

From the viewpoint of easy availability of raw materials and stability of the compound, the sulfur-containing cyclic hydrocarbon group is more preferably a 2-sulfolane or 3-sulfolane structure in which a ring including a sulfonyl group is a 5-membered ring, and among these, a 3-sulfolane structure is most preferable.

As the compound (1x), 3-sulfolanyl methacrylate is most preferable.

[High-Molecular-Weight Substance]

In the present embodiment, the content of the high-molecular-weight substance in the (meth)acrylic ester can be analyzed by a method described in the section of Examples described later, and the detection limit thereof is 0.03 mass % or less.

The high-molecular-weight substance in the (meth)acrylic ester according to the present embodiment is a high-molecular-weight substance produced by polymerizing or copolymerizing a (meth)acrylic ester having a sulfonyl group, which is a target substance (compound (1x)) in a step 1 of the production method of a (meth)acrylic ester described later, or a compound (3x) described later, which is a raw material for producing the compound (1x), due to their high polymerizable property. The molecular weight thereof is 5000 or more, and the weight average molecular weight (Mw) thereof measured by a method described in the section of Examples described later is approximately $3\times10^5$ to $6\times10^5$. In a case of a high-molecular-weight substance having a molecular weight of less than 5000, since the high-molecular-weight substance is soluble in a solvent, the high-molecular-weight substance remains in a mother liquor by recrystallization or the like to be removed. Therefore, the high-molecular-weight substance is not a target for removal in a step 2 described later.

The content of the high-molecular-weight substance in the (meth)acrylic ester according to the present embodiment is preferably small as much as 0.1 mass % or less, preferably 0.05 mass % or less, more preferably 0.03 mass % or less, and most preferably in an amount below the detection limit.

The (meth)acrylic ester according to the present embodiment, in which the content of the high-molecular-weight substance is reduced in this manner, can be produced by the production method of a (meth)acrylic ester according to the present embodiment described later.

[Application]

The (meth)acrylic ester according to the present embodiment, in which the content of the high-molecular-weight substance is reduced, can exhibit the original excellent properties of the sulfonyl group-containing (meth)acrylic ester without being affected by the high-molecular-weight substance. For example, the (meth)acrylic ester according to the present embodiment is useful for a wide range of applications such as plastic raw materials, paints, and adhesives.

In particular, the sulfonyl group-containing (meth)acrylic ester according to the present embodiment is useful for a resist application, for example, as a monomer constituting an ArF resist polymer. By using the monomer having a reduced content of the high-molecular-weight substance, lithography characteristics of the resist polymer can be improved. For example, solubility and developability of the resist polymer can be improved, and defects during development due to the high-molecular-weight substance can be prevented. In addition, due to the sulfonyl group, adhesiveness to a substrate and affinity for a polar solvent can be improved.

The sulfonyl group-containing (meth)acrylic ester according to the present embodiment can be suitably used as the above-described monomer (1) constituting the above-described polymer A.

<Production Method of (Meth)Acrylic Ester>

A production method of a (meth)acrylic ester according to the present embodiment is a method for producing the (meth)acrylic ester represented by Formula (1x), and includes the following steps 1 and 2.

Step 1: step of performing an ester exchange reaction between an alcohol represented by Formula (2x) and a (meth)acrylic ester represented by Formula (3x) to obtain a solution including a (meth)acrylic ester represented by Formula (1x)

In Formula (2x), $Z^{11}$ represents an atomic group forming a sulfur-containing cyclic hydrocarbon group having 3 to 6 carbon atoms, which includes a carbon atom bonded to a hydroxy group, and —$SO_2$—.

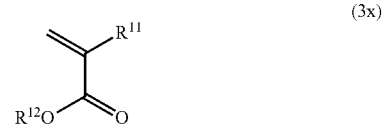

In Formula (3x), $R^{11}$ represents a hydrogen atom or a methyl group, and $R^{12}$ represents a linear or branched alkyl group having 1 to 10 carbon atoms.

Step 2: step of adding a poor solvent to the solution including the (meth)acrylic ester represented by Formula (1x) obtained in the step 1 to precipitate a high-molecular-weight substance, and removing the high-molecular-weight substance

[Step 1: Reaction Step]

In the step 1, the compound (1x) is obtained by reacting an alcohol compound (2x) represented by Formula (2x) with a (meth)acrylic ester compound (3x) represented by Formula (3x).

In the compound (2x), $Z^{11}$ is an atomic group forming a sulfur-containing cyclic hydrocarbon group having 3 to 6 carbon atoms, which includes a carbon atom bonded to a hydroxy group, and —$SO_2$—. From the viewpoint of the stability of the cyclic structure, the sulfur-containing cyclic hydrocarbon group preferably has 4 to 6 carbon atoms. In addition, a substituent may be bonded to a carbon atom constituting a ring of the sulfur-containing cyclic hydrocarbon group. Examples of the substituent include a linear or branched alkyl group having 1 to 10 carbon atoms, a hydroxy group, an amino group, an aldehyde group, a chloro group, a bromo group, and an iodo group.

From the viewpoint of easy availability of raw materials, the sulfur-containing cyclic hydrocarbon group is more preferably a 2-sulfolane or 3-sulfolane structure in which a ring including a sulfonyl group is a 5-membered ring. Among these, a 3-sulfolane structure is most preferable.

As the compound (2x), 3-hydroxysulfolane is most preferable.

In the compound (3x), $R^{11}$ is a hydrogen atom or a methyl group, and is preferably a methyl group.

$R^{12}$ is a linear or branched alkyl group having 1 to 10 carbon atoms. Examples of the linear or branched alkyl group having 1 to 10 carbon atoms include a methyl group, an ethyl group, an n-propyl group, an isopropyl group, an n-butyl group, an isobutyl group, a t-butyl group, an n-pentyl group, an n-hexyl group, and a 2-ethylhexyl group.

In the ester exchange reaction, since it is necessary to remove alcohol derived from the raw material ester by distillation, it is preferable that the boiling point of the by-product alcohol produced by the ester exchange reaction be low. From this viewpoint, $R^{12}$ is preferably a methyl group.

That is, as the compound (3x), methyl acrylate or methyl methacrylate is preferable.

In the step 1, the compound (1x) is produced by the ester exchange reaction. Conditions of the ester exchange reaction are not particularly limited, and a known method may be performed. For example, Japanese Unexamined Patent Application, First Publication No. 2007-153763 discloses a method of obtaining 3-sulfolanyl methacrylate by reacting 3-hydroxysulfolane with methyl methacrylate.

In order to obtain the compound (1x) in good yield, it is preferable to dehydrate the compound (2x) before use. As a dehydration method, a method in which the compound (2x) is dissolved in an organic solvent and then heated, and water is removed by azeotropy of the organic solvent and water is preferable. As the azeotropic organic solvent, benzene, toluene, ethylbenzene, methylethylketone, 1,4-dioxane, hexane, cyclohexane, or the like can be used. In addition, when the compound (3x) is azeotropically boiled with water, it is also possible to perform the dehydration by dissolving the compound (2x) in the compound (3x) and then azeotropically boiling.

In the ester exchange reaction, a catalyst may or may not be used. In order to obtain the compound (1x) in good yield, it is preferable to use a catalyst. When a catalyst is used, a titanium catalyst or a tin catalyst can be used. Examples of the titanium catalyst include titanium tetramethoxide, titanium tetraethoxide, titanium tetra-n-propoxide, titanium tetraisopropoxide, titanium tetra-n-butoxide, and titanium tetraisobutoxide. Examples of the tin catalyst include di-n-butyltin oxide, di-n-octyltin oxide, and di-2-ethylhexyltin oxide. From the viewpoint of catalyst removability after reaction, it is preferable to use the titanium catalyst.

From the viewpoint of efficiently obtaining the compound (1x), the amount of the catalyst used is preferably 0.001 mol or more and more preferably 0.01 mol or more with respect to 1 mol of the compound (2x). In addition, from the viewpoint of catalyst removability and cost, the amount of the catalyst used is preferably 0.05 mol or less and more preferably 0.03 mol or less with respect to 1 mol of the compound (2x). The ester exchange catalyst may be added all at once or may be added in divided portions.

For example, the amount of the catalyst used is preferably 0.001 to 0.05 mol and more preferably 0.01 to 0.03 mol with respect to 1 mol of the compound (2x).

The amount of the compound (3x) used in the ester exchange reaction is not particularly limited, but from the viewpoint of obtaining the compound (1x) in good yield, the amount thereof is preferably 0.5 mol or more, more preferably 0.8 mol or more, and still more preferably 1.0 mol or more with respect to 1 mol of the compound (2x). In particular, when the by-product alcohol is removed by azeotropy with the compound (3x), since the by-product alcohol cannot be sufficiently removed when the amount of the compound (3x) used is small, the reaction rate may decrease. In addition, from the viewpoint of suppressing pot efficiency of the ester exchange reaction and load on the treatment steps after the reaction, the amount of the compound (3x) used is preferably 12 mol or less, more preferably 10 mol or less, and still more preferably 8 mol or less with respect to 1 mol of the compound (2x).

For example, the amount of the compound (3x) used is preferably 0.5 to 12 mol, more preferably 0.8 to 10 mol, and still more preferably 1 to 8 mol with respect to 1 mol of the compound (2x).

In order to suppress polymerization of the compound (3x) or the compound (1x), it is preferable to add a polymerization inhibitor to the reaction system. The type of the polymerization inhibitor is not particularly limited, and one type may be used or two or more types may be used.

Examples of the polymerization inhibitor include phenolic compounds such as hydroquinone, p-methoxyphenol, 2,4-dimethyl-6-tert-butylphenol, 2,6-tert-butyl-4-methylphenol, tert-butylcatechol, and 2,6-di-tert-butyl-4-methylphenol; amine compounds such as N,N-diisopropyl-p-phenylenediamine, N-(1,3-dimethylbutyl)-N'-phenyl-p-phenylenediamine, and N,N-di-2-naphthylparaphenylenediamine; and N-oxyl compounds such as 4-hydroxy-2,2,6,6-tetramethylpiperidin-N-oxyl, 4-benzoyloxy-2,2,6,6-tetramethylpiperidin-N-oxyl, 4-acetamido-2,2,6,6-tetramethylpiperidin-N-oxyl, and bis(1-oxyl-2,2,6,6-tetramethylpiperidin-4-yl) sebacate.

In addition, in order to prevent the polymerization, it is also preferable to perform bubbling with an oxygen-containing gas during the ester exchange reaction. The amount of the oxygen-containing gas to be introduced can be set as appropriate. It is particularly preferable to use air as the oxygen-containing gas.

The temperature of the ester exchange reaction is not particularly limited, but in order to remove the by-product alcohol and improve the reaction rate, the temperature is preferably 30° C. or higher and more preferably 60° C. or higher. In addition, in order to suppress polymerization of the compound (3x) or the compound (1x), the temperature is preferably 160° C. or lower and more preferably 140° C. or lower.

For example, the temperature of the ester exchange reaction is preferably 30° C. to 160° C. and more preferably 60° C. to 140° C.

From the viewpoint of efficiently obtaining the compound (1x), the time of the ester exchange reaction is preferably 0.5 hours or more and more preferably 1 hour or more. In addition, in order to suppress polymerization of the compound (3x) or the compound (1x), the time is preferably 50 hours or less and more preferably 30 hours or less.

For example, the time of the ester exchange reaction is preferably 0.5 to 50 hours and more preferably 1 to 30 hours.

When a catalyst is used, as a post-treatment after the reaction, an operation of deactivating the catalyst may be performed. In particular, when the compound (1x) is used for a resist, it is preferable to reduce metal contamination as much as possible. Therefore, when a metal is used as the catalyst, it is preferable to deactivate and remove the catalyst. An example of a method thereof includes the following method.

That is, after cooling the reaction solution to approximately 70° C. or lower with stirring, the same amount or more of water as the added catalyst, an adsorbent, and Celite as a filtration aid are added thereto, so that the catalyst is turned into a metal oxide to be deactivated and precipitated. After the addition is completed, stirring is continued for approximately 1 to 5 hours. The precipitated metal oxide can be removed by pressure filtration, filtration under reduced pressure, or the like.

[Step 2: Purification Step]

In the step 2, a poor solvent is added to the solution including the compound (1x) produced in the step 1 to precipitate a high-molecular-weight substance, and the precipitated high-molecular-weight substance is removed. The precipitation of the high-molecular-weight substance by the poor solvent in the step 2 is to precipitate the high-molecular-weight substance without precipitating the compound (1x), which is different from a washing operation and a recrystallization operation described later in which the high-molecular-weight substance is not precipitated.

The poor solvent to be added is not particularly limited, and examples thereof include hydrocarbon solvents such as pentane, hexane, heptane, cyclopentane, cyclohexane, octane, toluene, and xylene; ether solvents such as diethyl ether, diisopropyl ether, t-butylmethyl ether, tetrahydrofuran, and dioxane; ester solvents such as ethyl acetate, butyl acetate, methyl methacrylate, ethyl methacrylate, isopropyl methacrylate, and butyl methacrylate; and alcoholic solvents such as methanol, ethanol, and 2-propanol. One kind of the poor solvent may be used, or two or more kinds thereof may be mixed and used.

It is more preferable to use a hydrocarbon solvent having a low solubility of the high-molecular-weight substance. Among these, from the viewpoint that it is easy to remove by distillation or the like, a saturated hydrocarbon solvent having 5 to 7 carbon atoms such as pentane, hexane, and heptane is still more preferable.

The amount of the poor solvent added can be appropriately determined depending on the amount of the high-molecular-weight substance and the solubility. In order to lower the solubility of the high-molecular-weight substance to precipitate the high-molecular-weight substance, the amount of the poor solvent added is preferably 0.2 mass times or more and more preferably 0.5 mass times or more with respect to the mass of the compound (2x) used in the reaction. In addition, from the viewpoint of economic efficiency and pot efficiency, the amount of the poor solvent added is preferably 5 mass times or less and more preferably 3 mass times or less with respect to the mass of the compound (2x) used in the reaction.

For example, the amount of the poor solvent added is preferably 0.2 to 5 mass times and more preferably 0.5 to 3 mass times with respect to the mass of the compound (2x) used in the reaction.

The method for removing the precipitated high-molecular-weight substance is not particularly limited, and examples thereof include separation as distillation residue, pressure filtration, filtration under reduced pressure, and centrifugation. An appropriate method may be used in consideration of the boiling point and properties of the compound (1x), scale, the amount of the high-molecular-weight substance, and the like. In order to prevent the formation of the high-molecular-weight substance again in the process of removal, it is desirable to use pressure filtration, filtration under reduced pressure, or centrifugation, which is a non-heating method.

After the separation of the high-molecular-weight substance, the poor solvent may be removed by concentration by vacuum distillation or the like.

The step 2 may include a purification operation of the compound (1x) as necessary. Examples of the method for purifying the compound (1x) include washing, heat treatment, filtration, distillation, and recrystallization. These may be performed individually, or may be performed in combination of two or more thereof. The purification may be performed before or after the precipitation step of the high-molecular-weight substance, or may be performed both before and after.

Since the compound (2x) has a sulfonyl group, the compound (2x) has high polarity and is easily dissolved in water. Therefore, by washing with, as a washing solution, water or an aqueous solution in which 5 to 30 mass % of inorganic salts such as sodium chloride, ammonium sulfate, and sodium sulfate are dissolved, the compound (2x) can be removed into the aqueous layer. The number of washings can be appropriately determined. From the viewpoint of reducing contamination of metal in the compound (1x), it is preferable to include a step of washing with water.

The above-described washing may be performed without adding a solvent, or may be performed by diluting with a solvent. In order to reduce hydrolysis of the compound (1x) and outflow to the aqueous layer, it is preferable to dilute with a solvent. The solvent is not particularly limited, and examples thereof include hydrocarbon solvents such as pentane, hexane, heptane, cyclopentane, cyclohexane, octane, toluene, and xylene; ether solvents such as diethyl ether, diisopropyl ether, t-butylmethyl ether, tetrahydrofuran, and dioxane; and ester solvents such as ethyl acetate, butyl acetate, methyl methacrylate, ethyl methacrylate, isopropyl methacrylate, and butyl methacrylate. One kind of these solvents may be used, or two or more kinds thereof may be mixed and used. The amount of the solvent to be used can be appropriately determined depending on solubility of the compound (1x) and the amount of the washing solution.

When the compound (1x) is purified by distillation, it is preferable to perform the distillation by adding the polymerization inhibitor and appropriately introducing the oxygen-containing gas such as air at a vacuum degree of 1.3 kPa (10 mmHg) or less. In particular, from the viewpoint that heat history is less, it is preferable to perform the distillation by a method such as thin film distillation.

When the compound (1x) is purified by recrystallization, a solvent in which the above-described compound (1x) is dissolved at room temperature to 40° C. and crystals are precipitated by cooling below room temperature is used. As the solvent used for the recrystallization, alcoholic solvents such as methanol, ethanol, isopropanol, and butanol, ester solvents such as ethyl acetate, butyl acetate, and methyl methacrylate, and ether solvents such as diethyl ether, diisopropyl ether, and t-butylmethyl ether can be used alone, or can be mixed and used. In addition, in order to improve the recovery rate of the recrystallization, a hydrocarbon solvent such as hexane, octane, and heptane, a halogen solvent such as dichloroethane and dichloromethane, water, or the like, in which is difficult to dissolve the crystals, can also be used by mixing with the above-described alcoholic solvent, the above-described ester solvent, or the above-described ether solvent. From the viewpoint that the solvent can be easily reused, it is preferable to use the alcoholic solvent alone. In addition, from the viewpoint of improving the recovery rate by adjusting the slurry concentration when the crystals are precipitated, a mixed solvent of the alcoholic solvent and the hydrocarbon solvent is more preferable.

From the viewpoint of suppressing an increase in viscosity and improving process passability, the slurry concentration is preferably 25 mass % or less and more preferably 20 mass % or less. In addition, from the viewpoint of economic efficiency and pot efficiency, the slurry concentration is preferably 5 mass % or more and more preferably 10 mass % or more.

For example, the slurry concentration is preferably 5 to 25 mass % and more preferably 10 to 20 mass %.

In the recrystallization, it is preferable to promote crystallization by dissolving the compound (1x) in a solvent at 30° C. or higher, gradually cooling the solution, and adding seed crystals when the internal temperature reached 5° C. to 10° C. With the crystallization, the internal temperature increases due to latent heat, but when the solution is cooled and the internal temperature reached 10° C. or lower, the crystals are separated. The separation of the crystals can be performed using a centrifugal filter, a pressure filter, or the like. After the separation of the crystals, the crystals are washed with a solvent.

After the recrystallization, it is preferable that the crystals be separated using a solvent which is mixed or dissolved in water, and then the wet crystal cake be washed with water. As a result, most of the solvent adhering to the crystals can be removed, and even when the temperature of the wet crystals increases to around room temperature, there is almost no possibility of melting.

EXAMPLES

Hereinafter, the present invention will be described in more detail with reference to Examples, but the present invention is not limited to these examples.

Example (I)

Reaction tracking was performed by gas chromatography.
<Measurement Method of Weight Average Molecular Weight>

The weight average molecular weight (Mw) and molecular weight distribution (Mw/Mn) of a polymer were determined by gel permeation chromatography in terms of polystyrene. As an eluent, tetrahydrofuran (THF) was used.
<Measurement Method of Copolymerization Composition Ratio>

With regard to polymers obtained in each example, a composition ratio (unit: mol %) of constituent units based on each monomer was determined by $^1$H-NMR measurement.

In the measurement, using an ECS-400 type superconducting Fourier Transformation (FT)-NMR device manufactured by JEOL Ltd., approximately 5 mass % of a sample solution (solvent was deuterated chloroform) was placed in a sample tube having a diameter of 5 mmφ, and integration was performed 64 times in a single pulse mode with an observation frequency of 400 MHz. The measurement temperature was 60° C.
<Evaluation Method of Solubility in Developer (Measurement Method of Turbidity)>

Using a turbidimeter (manufactured by Orbeco-Hellige, Inc., product name: TB200), a turbidity Th(80) and a turbidity Tm(80) were measured by the following methods.

The Th(80) is an index of solubility in a low-polarity organic solvent, and the Tm(80) is an index of solubility in a high-polarity organic solvent. As the turbidity becomes higher, the solubility in an organic solvent becomes lower. In other words, as the turbidity becomes higher, the polarity becomes higher and the solubility in an alkaline developer is excellent.

[Measurement Method of Turbidity Th(80)]

(1) a polymer to be measured was dissolved in a mixed solvent of PGMEA/γ-butyrolactone=75/25 mass % to prepare a PGMEA/γ-butyrolactone solution (hereinafter, referred to as a sample solution) having a concentration of 20 mass %.

(2) n-heptane was added to the sample solution prepared in (1) to prepare a mixed solution, and the amount of n-heptane added (Xh mass %) to the sample solution when the turbidity of the mixed solution reached 10 NTU was determined.

(3) an amount of n-heptane corresponding to 80% of Xh mass % was added to the sample solution prepared in (1), and the mixture was stirred at 25° C. for 4 hours to obtain a measurement solution.

(4) turbidity of the measurement solution at 25° C. was defined as Th(80).

[Measurement Method of Turbidity Tm(80)]

(5) methanol was added to the sample solution prepared in (1) to prepare a mixed solution, and the amount of methanol added (Xm mass %) to the sample solution when the turbidity of the mixed solution reached 5.0 NTU was determined.

(6) an amount of methanol corresponding to 80% of Xm mass % was added to the sample solution prepared in (1), and the mixture was stirred at 25° C. for 4 hours to obtain a measurement solution.

(7) turbidity of the measurement solution at 25° C. was defined as Tm(80).

In the following examples and comparative examples, the following monomers (m1) to (m7) were used.

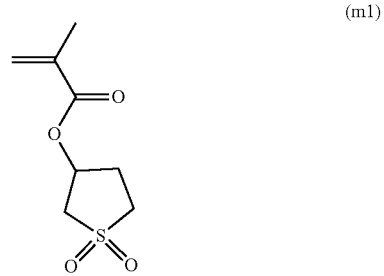

(m1)

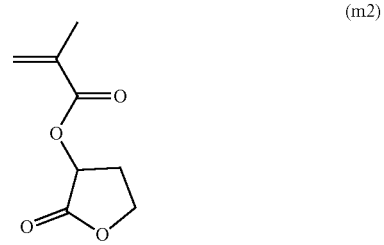

(m2)

(m3)

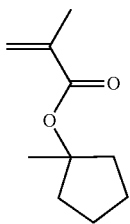

(m4)

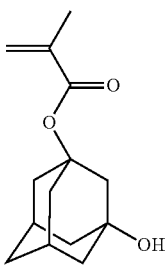

(m5)

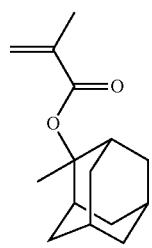

(m6)

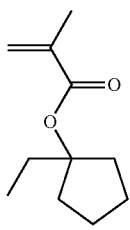

(m7)

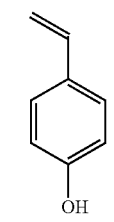

Example 1-1

Into a flask equipped with a nitrogen inlet, a stirrer, a condenser, and a thermometer, 8.1 parts by mass of PGMEA and 32.5 parts by mass of γ-butyrolactone were charged in a nitrogen atmosphere, and the temperature of a hot water bath was raised to 80° C. while stirring the mixture. Thereafter, the following mixture 1 was added dropwise to the flask from a dropping funnel over 4 hours, and the temperature was further maintained at 80° C. for 3 hours to obtain a reaction solution.

(Composition of Mixture 1)

Monomer (m1): 8.17 parts by mass (20 mol %),
Monomer (m2): 10.20 parts by mass (30 mol %),
Monomer (m3): 13.44 parts by mass (40 mol %),
Monomer (m4): 4.72 parts by mass (10 mol %),
Solvent: 8.9 parts by mass of PGMEA and 35.7 parts by mass of γ-butyrolactone, and
Polymerization initiator: 3.91 parts by mass of dimethyl-2,2'-azobisisobutyrate (manufactured by Wako Pure Chemical Corporation, V601 (trade name))

The obtained reaction solution was added dropwise to a mixed solvent of methanol and water (methanol/water=80/20 volume ratio) in an amount of approximately 10 times while stirring to obtain a white precipitate. The precipitate was separated by filtration, and poured again into methanol in the same amount as described above to be washed while stirring. The precipitate after washing was filtered off to obtain a polymer wet powder, and the polymer wet powder was dried under reduced pressure at 60° C. for approximately 36 hours to obtain a dry powdery polymer.

The weight average molecular weight (Mw) and molecular weight distribution (Mw/Mn) of the obtained polymer are shown in Table 1 (the same applies hereinafter).

With regard to the obtained polymer, the turbidity was measured by the above-described method. The results are shown in Table 1 (the same applies hereinafter).

The copolymerization composition ratio shown in Table 1 is a charging ratio, but when the copolymerization composition ratio of the obtained polymer was measured by the above-described method, the constituent unit (m1) was 20.2 mol %, the constituent unit (m2) was 30.1 mol %, the constituent unit (m3) was 39.7 mol %, and the constituent unit (m4) was 10.0 mol %, which were almost the same as the charging ratio.

15.0 parts by mass of the dry powdery polymer obtained above, 105.0 parts by mass of PGMEA, and 0.3 parts by mass of triphenylsulfonium triflate, which is a photoacid generator, were mixed to a uniform solution, and then the mixture was filtered with a membrane filter having a pore size of 0.1 μm to produce a resist composition.

Example 1-2 and Comparative Example 1-1

The charged composition of the monomer in Example 1-1 was changed as shown in Table 1. Polymers were produced and evaluated in the same manner as in Example 1-1.

In addition, using the obtained polymers, resist compositions were produced in the same manner as in Example 1-1.

Comparative Examples 2-1 and 2-2

The charged composition of the monomer in Example 1-1 was changed as shown in Table 1. Polymers were produced and evaluated in the same manner as in Example 1-1.

In addition, using the obtained polymers, resist compositions were produced in the same manner as in Example 1-1.

Examples 3-1 and 4-1, and Comparative Example 3-1

The charged composition of the monomer in Example 1-1 was changed as shown in Table 1. Polymers were produced and evaluated in the same manner as in Example 1-1.

In addition, using the obtained polymers, resist compositions were produced in the same manner as in Example 1-1.

TABLE 1

| | Composition of monomer (molar ratio) | | | | | | | Molecular weight | | Turbidity (NTU) | |
|---|---|---|---|---|---|---|---|---|---|---|---|
| | m1 | m2 | m3 | m4 | m5 | m6 | m7 | Mw | Mw/Mn | Th(80) | Tm(80) |
| Example 1-1 | 20 | 30 | 40 | 10 | — | — | — | 9700 | 1.76 | 6.9 | 4.4 |
| Example 1-2 | 60 | — | 40 | — | — | — | — | 9700 | 1.77 | 6.4 | 4.0 |
| Comparative Example 1-1 | — | 60 | 40 | — | — | — | — | 9600 | 1.80 | 4.0 | 3.4 |
| Comparative Example 2-1 | 20 | 30 | — | 10 | 40 | — | — | 9500 | 1.82 | 5.3 | 3.6 |
| Comparative Example 2-2 | 60 | — | — | — | 40 | — | — | 9600 | 1.79 | 5.5 | 3.6 |
| Example 3-1 | 20 | 30 | 20 | — | 30 | — | — | 9800 | 1.78 | 5.7 | 3.7 |
| Comparative Example 3-1 | 20 | 30 | 10 | — | 40 | — | — | 9700 | 1.77 | 5.4 | 3.5 |
| Example 4-1 | 30 | — | — | — | — | 40 | 30 | 9700 | 1.80 | 7.3 | 4.4 |

As shown in Table 1, since the polymers of Examples 1-1, 1-2, 3-1, and 4-1 had high turbidity, the polymers had high polarity and had excellent solubility in an alkaline developer.

Example (II)

In the following examples and comparative examples, 3-hydroxysulfolane synthesized according to the method of Patent Document 1 (Japanese Unexamined Patent Application, First Publication No. 2007-153763) was used.

As methyl methacrylate, ACRYESTER M (product name) manufactured by Mitsubishi Chemical Corporation was used.

As titanium tetrabutoxide, titanium tetrabutoxide manufactured by KANTO CHEMICAL CO., INC. was used.

As 4-hydroxy-2,2,6,6-tetramethylpiperidin-N-oxyl, 4-hydroxy-2,2,6,6-tetramethylpiperidin-N-oxyl manufactured by Fujifilm Wako Pure Chemical Corporation was used.

As Celite, Celite 545 (product name) manufactured by Kishida Chemical Co., Ltd. was used.

The reaction rate in the ester exchange reaction was calculated by the following expression from a peak area measured by a gas chromatograph (hereinafter, referred to as "GC"; equipment: Agilent 6890GC of Agilent Technologies, Inc., column: HP-5).

Reaction rate (%)=(A/B)×100

Here, A represents a quantitative value of a compound (1) by a calibration curve, and B represents the total of quantitative values of the compound (1) and a compound (2) by the calibration curve.

The content of the high-molecular-weight substance was calculated by a quantitative value by a calibration curve from a peak area value measured by gel permeation chromatography (hereinafter, referred to as "GPC"; equipment: HLC-8320GPC of Tosoh Corporation, column: Shodex LF-804 (3 pieces), eluent: tetrahydrofuran).

The weight average molecular weight (Mw) of the high-molecular-weight substance was calculated from an elution time measured by GPC (equipment: HLC-8320GPC of Tosoh Corporation, column: Shodex LF-804 (3 pieces), eluent: tetrahydrofuran) using a calibration curve with standard polystyrene.

Example 5-1

[Step 1]

Into a 100 mL glass flask equipped with Dean-Stark, 20.1 g (147 mmol) of 3-hydroxysulfolane, 103.1 g (1.0 mol) of methyl methacrylate, and 0.12 g of 4-hydroxy-2,2,6,6-tetramethylpiperidin-1-oxyl (hereinafter, referred to as "HO-TEMPO") were charged, the solution was heated to reflux, and the water content in the solution was removed by the Dean-Stark. Next, 1.5 g (4 mmol) of titanium tetrabutoxide was added thereto, and while blowing air at 20 mL/min, the reaction solution was heated to reflux at an internal temperature of 100° C. to 110° C. While methanol produced by the reaction was removed by azeotropy with the methyl methacrylate using the Dean-Stark, the reaction solution was stirred for 2.5 hours. The amount of the mixed solution of methanol and methyl methacrylate extracted during this period was 45.8 g. The reaction rate by GC analysis was 91%. Thereafter, after cooling to room temperature, 1.6 g of water and 6.9 g of Celite were added thereto, the mixture was stirred for 1 hour, and the obtained mixed solution was filtered under reduced pressure with a filter paper. When GPC analysis and Mw measurement were performed, 1.15 mass % of a high-molecular-weight substance of Mw $4.6 \times 10^5$ was detected.

[Step 2]

30 mL of toluene was added to the obtained filtrate, 15 mL of water was added to wash the organic layer, and the aqueous layer was discharged using a separatory funnel. Thereafter, 20 mL of water was added to wash the organic layer, and the aqueous layer was discharged using a separatory funnel. Next, 24 g of hexane was added thereto, and the mixture was stirred to precipitate a gel-like high-molecular-weight substance. After adding magnesium sulfate to dry, the mixture was filtered under reduced pressure using a filter paper, and the filtrate was concentrated using an evaporator to obtain 22.1 g of crude 3-sulfolanyl methacrylate. As a result of GPC analysis, no high-molecular-weight substance having a molecular weight of 5000 or more was detected.

66.2 g of 2-propanol and 33.1 g of heptane were added to the obtained crude 3-sulfolanyl methacrylate, the mixture was cooled while stirring, and seed crystals were added at a temperature below 20° C. to precipitate crystals. The obtained crystals were filtered, washed with heptane and water, and dried under reduced pressure to obtain 12.9 g of purified 3-sulfolanyl methacrylate. As a result of GPC analysis, no high-molecular-weight substance having a molecular weight of 5000 or more was detected.

Example 5-2

[Step 1]

Into a 3 L glass flask equipped with a stirrer, a thermometer, and Dean-Stark, 351 g (2.6 mol) of 3-hydroxysulfolane, 1770 g (17.7 mol) of methyl methacrylate, and 2.2 g of HO-TEMPO were charged, the solution was heated to reflux, and the water content in the solution was removed by the Dean-Stark. Next, 26 g (77 mmol) of titanium tetrabutoxide was added thereto, and while blowing air at 20 mL/min, the reaction solution was heated to reflux at an internal temperature of 100° C. to 110° C. While methanol produced by the reaction was removed by azeotropy with the methyl methacrylate using the Dean-Stark, the reaction solution was stirred for 8 hours. The amount of the mixed solution of methanol and methyl methacrylate extracted during this period was 902 g. The reaction rate by GC analysis was 88%. Thereafter, after cooling to room temperature, 28 g of water and 121 g of Celite were added thereto, the mixture was stirred for 1 hour, and the obtained mixed solution was filtered under reduced pressure with a filter paper. When GPC analysis and Mw measurement were performed, 0.08 mass % of a high-molecular-weight substance of Mw $4.0 \times 10^5$ was detected.

[Step 2]

900 mL of toluene was added to the obtained filtrate and 200 mL of water was added to wash the organic layer, so that 242 g of the aqueous layer was separated. Next, 200 mL of water was added to wash the organic layer, so that 204 g of the aqueous layer was separated. Next, 650 mL of hexane was added thereto, and the mixture was stirred to precipitate a gel-like high-molecular-weight substance. After adding magnesium sulfate to dry, the mixture was filtered under reduced pressure using a filter paper, and the filtrate was concentrated using an evaporator to obtain 406 g of crude 3-sulfolanyl methacrylate. As a result of GPC analysis, no high-molecular-weight substance having a molecular weight of 5000 or more was detected.

While keeping the obtained crude 3-sulfolanyl methacrylate at 26° C., 1181 g of 2-propanol and 592 g of heptane were added thereto, the mixture was cooled while stirring, and seed crystals were added at a temperature below 20° C. to precipitate crystals. The obtained crystals were filtered, washed with heptane and water, and dried under reduced pressure to obtain 219 g of purified 3-sulfolanyl methacrylate. As a result of GPC analysis, no high-molecular-weight substance having a molecular weight of 5000 or more was detected.

Example 5-3

[Step 1]

Into a 10 L glass separable flask equipped with a stirrer, a thermometer, and Dean-Stark, 1394 g (10.2 mol) of 3-hydroxysulfolane, 7269 g (72.6 mol) of methyl methacrylate, and 4.4 g of HO-TEMPO were charged, the solution was heated to reflux, and the water content in the solution was removed by the Dean-Stark. Next, 70 g (0.2 mol) of titanium tetrabutoxide was added thereto, and while blowing air at 20 mL/min, the reaction solution was heated to reflux at an internal temperature of 100° C. to 110° C. While methanol produced by the reaction was removed by azeotropy with the methyl methacrylate using the Dean-Stark, the reaction solution was stirred for 6 hours. The amount of the mixed solution of methanol and methyl methacrylate extracted during this period was 1477 g. The reaction rate by GC analysis was 67%. Next, the reaction solution was cooled to 70° C. or lower, 35 g (0.1 mol) of titanium tetrabutoxide was added thereto, and while blowing air at 20 mL/min, the reaction solution was heated to reflux at an internal temperature of 100° C. to 110° C. While methanol produced by the reaction was removed by azeotropy with the methyl methacrylate using the Dean-Stark, the reaction solution was stirred for 7.5 hours. The amount of the mixed solution of methanol and methyl methacrylate extracted during this period was 2081 g. The reaction rate by GC analysis was 87%. The reaction solution was cooled to 70° C. or lower again, 3.5 g (0.01 mol) of titanium tetrabutoxide was added thereto, and while blowing air at 20 mL/min, the reaction solution was heated to reflux at an internal temperature of 100° C. to 110° C. The stirring was continued for 3.5 hours, but the reaction rate by GC analysis was 87%. The amount of the mixed solution of methanol and methyl methacrylate extracted during this period was 525 g. Thereafter, after cooling to 70° C. or lower, 16 g of water and 483 g of Celite were added thereto, the mixture was stirred for 1 hour, and the obtained mixed solution was filtered under pressure with a filter paper. When GPC analysis and Mw measurement were performed, 0.21 mass % of a high-molecular-weight substance of Mw $4.2 \times 10^5$ was detected.

[Step 2]

3000 g of toluene was added to the obtained filtrate and 812 g of water was added to wash the organic layer, so that 965 g of the aqueous layer was separated. Next, 837 g of water was added to wash the organic layer, so that 852 g of the aqueous layer was separated. Next, 2020 g of hexane was added thereto, and the mixture was stirred to precipitate a gel-like high-molecular-weight substance. The high-molecular-weight substance was removed by pressure filtration with a filter paper, and the filtrate was concentrated using an evaporator to obtain 1641 g of crude 3-sulfolanyl methacrylate. As a result of GPC analysis, no high-molecular-weight substance having a molecular weight of 5000 or more was detected.

While keeping the obtained crude 3-sulfolanyl methacrylate at 22° C., 4690 g of 2-propanol and 2380 g of heptane were added thereto, the mixture was cooled while stirring, and seed crystals were added at a temperature below 17° C. to precipitate crystals. The obtained crystals were filtered, washed with heptane and water, and dried under reduced pressure to obtain 1000 g of purified 3-sulfolanyl methacrylate. As a result of GPC analysis, no high-molecular-weight substance having a molecular weight of 5000 or more was detected.

Comparative Example 5-1

Using 20.0 g (147 mmol) of 3-hydroxysulfolane, 118.0 g (1.2 mol) of methyl methacrylate, 0.12 g of HO-TEMPO, and 0.7 g (4 mmol) of titanium tetraethoxide, the step 1 was performed in the same manner as in Example 5-1. When GPC analysis and Mw measurement of the filtrate were performed, 0.29 mass % of a high-molecular-weight substance of Mw $4.8 \times 10^5$ was detected.

30 mL of toluene was added to the obtained filtrate, 15 mL of water was added to wash the organic layer, and the aqueous layer was discharged using a separatory funnel. Thereafter, 15 mL of water was added to wash the organic layer, and the aqueous layer was discharged using a separatory funnel. After adding magnesium sulfate to dry, the mixture was filtered under reduced pressure using a filter paper, and the filtrate was concentrated using an evaporator to obtain 25.6 g of crude 3-sulfolanyl methacrylate. As a result of GPC analysis, 0.22 mass % of the high-molecular-weight substance was detected. When 38.9 g of 2-propanol was added to the crude 3-sulfolanyl methacrylate, a gel-like high-molecular-weight substance was precipitated, but in this state, 38.4 g of 2-propanol and 38.5 g of heptane were added thereto, and seed crystals were added at a temperature below 20° C. to perform recrystallization, thereby obtaining 21.3 g of purified 3-sulfolanyl methacrylate. As a result of analysis by GPC, 0.11 mass % of a high-molecular-weight substance having a molecular weight of 5000 or more was detected.

In these examples, the results of Mw measurement and GPC analysis of the high-molecular-weight substance in each step are shown in Table 2.

In Table 2, "After step 1" represents the analysis result after the reaction, "After step 2" represents the analysis result after adding the poor solvent to precipitate and remove the high-molecular-weight substance and concentrating the resultant, and "After recrystallization step" represents the analysis result of purified 3-sulfolanyl methacrylate obtained by the recrystallization purification.

N. D. means that the high-molecular-weight substance was not detected.

TABLE 2

| | | Content of high-molecular-weight substance (mass %) | |
|---|---|---|---|
| High-molecular-weight substance (Mw) | After step 1 | After step 2 | After recrystallization step |
| Example 5-1 | 4.6 × 10⁵ | 1.15 | N. D. | N. D. |
| Example 5-2 | 4.0 × 10⁵ | 0.08 | N. D. | N. D. |
| Example 5-3 | 4.2 × 10⁵ | 0.21 | N. D. | N. D. |
| Comparative Example 5-1 | 4.8 × 10⁵ | 0.29 | — | 0.11 |

As shown in the results in Table 2, the 3-sulfolanyl methacrylates obtained in Examples 5-1 to 5-3 were of high purity in which the high-molecular-weight substance having a molecular weight of 5000 or more was not detected.

Meanwhile, in Comparative Example 5-1 in which the step 2 was not performed, the obtained 3-sulfolanyl methacrylate contained 0.11 mass % of the high-molecular-weight substance having a molecular weight of 5000 or more.

From these results, it can be seen that a high-molecular-weight substance can be removed by precipitating a high-molecular-weight substance with a poor solvent in a purification step, and the content of the high-molecular-weight substance having a molecular weight of 5000 or more can be reduced to 0.1 mass % or less.

INDUSTRIAL APPLICABILITY

According to the present embodiment, a polymer having favorable solubility in a developer, a resist composition including the polymer, and a method for manufacturing a substrate having a pattern formed therein using the resist composition are obtained.

According to the present embodiment, a sulfonyl group-containing (meth)acrylic ester in which a high-molecular-weight substance is reduced is obtained.

In the (meth)acrylic ester according to the present embodiment, the content of the high-molecular-weight substance is reduced, and the (meth)acrylic ester according to the present embodiment is useful for a wide range of applications such as plastics, paints, and adhesives. In addition, the (meth)acrylic ester according to the present embodiment is suitable as a monomer constituting a resist polymer, and is useful for improving lithography characteristics.

The invention claimed is:

1. A (meth)acrylic ester represented by Formula (1x), wherein a content of a high-molecular-weight substance having a molecular weight of 5000 or more is 0.03 mass % or more and 0.1 mass % or less, in Formula (1x), $R^{11}$ represents a hydrogen atom or a methyl group, $A^{11}$ represents a linking group including an ester bond, or a single bond, where $A^{11}$ has no tertiary carbon atom, and $Z^{11}$ represents an atomic group forming a sulfur-containing cyclic hydrocarbon group having 4 carbon atoms, which includes a carbon atom bonded to $A^{11}$, and —$SO_2$—

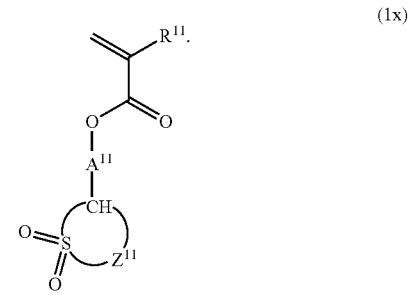

2. The (meth)acrylic ester according to claim 1, wherein in Formula (1x), $R^{11}$ represents the hydrogen atom.

3. The (meth)acrylic ester according to claim 1, wherein in Formula (1x), $R^{11}$ represents the methyl group.

4. The (meth)acrylic ester according to claim 1, wherein in Formula (1x), $A^{11}$ represents the linking group including the ester bond.

5. The (meth)acrylic ester according to claim 1, wherein in Formula (1x), $A^{11}$ represents the linking group including the single bond.

6. The (meth)acrylic ester according to claim 1, wherein the (meth)acrylic ester represented by Formula (1x) comprises a compound of the following formula:

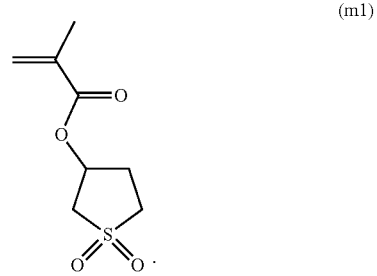

7. The (meth)acrylic ester according to claim 1, wherein the sulfur-containing cyclic hydrocarbon group having 4 carbon atoms is substituted with at least one substituent selected from the group consisting of a linear or branched alkyl group having 1 to 10 carbon atoms, a hydroxy group, an amino group, an aldehyde group, a chloro group, a bromo group and an iodo group.

8. The (meth)acrylic ester according to claim 1, wherein the content of a high-molecular-weight substance having the molecular weight of 5000 or more is 0.05 mass % or less.

9. The (meth)acrylic ester according to claim 1, wherein the sulfur-containing cyclic hydrocarbon group having 4 carbon atoms is substituted with a linear or branched alkyl group having 1 to 10 carbon atoms.

10. The (meth)acrylic ester according to claim 1, wherein the sulfur-containing cyclic hydrocarbon group having 4 carbon atoms is substituted with a hydroxy group.

11. The (meth)acrylic ester according to claim 1, wherein the sulfur-containing cyclic hydrocarbon group having 4 carbon atoms is substituted with an amino group.

12. The (meth)acrylic ester according to claim 1, wherein the sulfur-containing cyclic hydrocarbon group having 4 carbon atoms is substituted with an aldehyde group.

13. The (meth)acrylic ester according to claim 1, wherein the sulfur-containing cyclic hydrocarbon group having 4 carbon atoms is substituted with a chloro group.

14. The (meth)acrylic ester according to claim 1, wherein the sulfur-containing cyclic hydrocarbon group having 4 carbon atoms is substituted with a bromo group.

15. The (meth)acrylic ester according to claim 1, wherein the sulfur-containing cyclic hydrocarbon group having 4 carbon atoms is substituted with and an iodo group.

16. A production method of a (meth)acrylic ester represented by Formula (1x) according to claim 1, comprising:
    a step 1: step of performing an ester exchange reaction between an alcohol represented by Formula (2x) and a (meth)acrylic ester represented by Formula (3x) to obtain a solution including a (meth)acrylic ester (1x) represented by Formula (1x); and
    a step 2: step of adding a poor solvent to the solution including the (meth)acrylic ester (1x) obtained in the step 1 to precipitate a high-molecular-weight substance, and removing the high-molecular-weight substance, in Formula (1x), $R^{11}$ represents a hydrogen atom or a methyl group, $A^{11}$ represents a linking group including an ester bond, or a single bond, where $A^{11}$ has no tertiary carbon atom, and $Z^{11}$ represents an atomic group forming a sulfur-containing cyclic hydrocarbon group having 4 carbon atoms, which includes a carbon atom bonded to $A^{11}$, and $-SO_2-$, in Formula (2x), $Z^{11}$ represents an atomic group forming a sulfur-containing cyclic hydrocarbon group having 4 carbon atoms, which includes a carbon atom bonded to a hydroxy group, and $-SO_2-$, and in Formula (3x), $R^{11}$ represents a hydrogen atom or a methyl group, and $R^{12}$ represents a linear or branched alkyl group having 1 to 10 carbon atoms

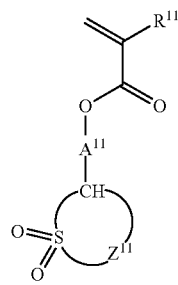

(1x)

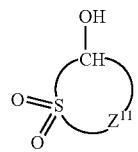

(2x)

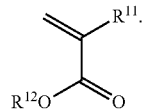

(3x)

17. The production method of a (meth)acrylic ester according to claim 16,
    wherein a hydrocarbon solvent is used as the poor solvent in step 2.

* * * * *